(12) United States Patent
Jaramaz et al.

(10) Patent No.: US 10,918,440 B2
(45) Date of Patent: Feb. 16, 2021

(54) SYSTEM AND METHODS FOR POSITIONING BONE CUT GUIDE

(71) Applicant: BLUE BELT TECHNOLOGIES, INC., Plymouth, MN (US)

(72) Inventors: Branislav Jaramaz, Pittsburgh, PA (US); Constantinos Nikou, Monroeville, PA (US)

(73) Assignee: Blue Belt Technologies, Inc., Pittsburgh, PA (US)

( * ) Notice: Subject to any disclaimer, the term of this patent is extended or adjusted under 35 U.S.C. 154(b) by 180 days.

(21) Appl. No.: 16/016,541

(22) Filed: Jun. 22, 2018

(65) Prior Publication Data

US 2018/0296276 A1    Oct. 18, 2018

Related U.S. Application Data

(62) Division of application No. 14/634,363, filed on Feb. 27, 2015, now abandoned.

(Continued)

(51) Int. Cl.
*A61B 34/10* (2016.01)
*G16H 50/50* (2018.01)
(Continued)

(52) U.S. Cl.
CPC .............. *A61B 34/10* (2016.02); *A61B 17/15* (2013.01); *A61B 17/17* (2013.01); *A61B 34/20* (2016.02);
(Continued)

(58) Field of Classification Search
CPC .............. A61B 34/10–108; A61B 17/155–158
See application file for complete search history.

(56) References Cited

U.S. PATENT DOCUMENTS 4,524,766 A * 6/1985 Petersen .............. A61B 17/154 606/184
4,759,350 A * 7/1988 Dunn .................... A61B 17/154 606/82

(Continued)

FOREIGN PATENT DOCUMENTS

EP    1669033 B1    2/2009
WO    2006136955 A1    12/2006
(Continued)

OTHER PUBLICATIONS

Chao et al. "Simulation and Animation of Musculosketal Joint System" (Nov. 1, 1993) J. Biomechanical Engineering 115(4B): 562-568.

(Continued)

*Primary Examiner* — Zade Coley
(74) *Attorney, Agent, or Firm* — Troutman Pepper Hamilton Sanders LLP

(57) ABSTRACT

Systems and methods for positioning a cut guide using navigation-based techniques are discussed. For example, a system for use in an orthopedic surgery on a target bone can comprise a cut guide adjustably positionable onto the target bone via two or more coupling receptacles created on the target bone. The coupling receptacles can include one or more guide members and a plurality of landing members. The system also includes an input interface that can receive a target bone representation, and a model receiver module that can receive a generic post-coupling bone model. The target bone representation can include a data set representing two or more landing sites of the target bone, and the generic post-coupling bone model can include a data set representing a bone having two or more coupling receptacles each sized, shaped or otherwise configured to receive and secure the respective coupling feature of the landing members. The system can include a navigation-based guide coupling (Continued)

preparation system that can generate a plan for positioning the cut guide onto or conforming to the target bone. The system can further include a display module that provides presentations of the coupling between the target bone and the cut guide.

19 Claims, 9 Drawing Sheets

Related U.S. Application Data

(60) Provisional application No. 61/946,428, filed on Feb. 28, 2014.

(51) Int. Cl.
*A61B 17/15* (2006.01)
*G16H 40/63* (2018.01)
*G16H 20/40* (2018.01)
*A61B 34/20* (2016.01)
*A61B 17/17* (2006.01)
*G16H 40/40* (2018.01)
*A61B 17/16* (2006.01)

(52) U.S. Cl.
CPC ............ *G16H 20/40* (2018.01); *G16H 40/40* (2018.01); *G16H 40/63* (2018.01); *G16H 50/50* (2018.01); *A61B 17/155* (2013.01); *A61B 17/16* (2013.01); *A61B 2034/105* (2016.02); *A61B 2034/107* (2016.02); *A61B 2034/108* (2016.02); *A61B 2034/2074* (2016.02)

(56) References Cited

U.S. PATENT DOCUMENTS

| | | | |
|---|---|---|---|
| 4,841,975 A | 6/1989 | Woolson | |
| 4,979,949 A | 12/1990 | Matsen, III et al. | |
| 5,086,401 A | 2/1992 | Glassman et al. | |
| 5,129,909 A * | 7/1992 | Sutherland | A61B 17/155 606/53 |
| 5,186,174 A * | 2/1993 | Schlondorff | A61B 6/501 378/4 |
| 5,344,423 A | 9/1994 | Dietz et al. | |
| 5,408,409 A * | 4/1995 | Glassman | A61B 34/20 600/407 |
| 5,474,559 A * | 12/1995 | Bertin | A61B 17/154 606/86 R |
| 5,494,034 A | 2/1996 | Schlondorff et al. | |
| 5,496,324 A | 3/1996 | Barnes | |
| 5,514,139 A * | 5/1996 | Goldstein | A61B 17/1764 606/79 |
| 5,571,110 A | 11/1996 | Matsen, III et al. | |
| 5,682,886 A | 11/1997 | Delp et al. | |
| 5,824,085 A | 10/1998 | Sahay et al. | |
| 5,880,976 A * | 3/1999 | DiGioia, III | A61F 2/4657 703/7 |
| 5,916,220 A | 6/1999 | Masini | |
| 6,205,411 B1 | 3/2001 | DiGioia, III et al. | |
| 6,711,432 B1 | 3/2004 | Krause et al. | |
| 6,757,582 B2 | 6/2004 | Brisson et al. | |
| 7,029,477 B2 | 4/2006 | Grimm | |
| 7,608,079 B1 | 10/2009 | Blackwell et al. | |
| 7,747,311 B2 | 6/2010 | Quaid, III | |
| 7,857,821 B2 | 12/2010 | Couture et al. | |
| 8,282,646 B2 | 10/2012 | Schoenefeld et al. | |
| 8,425,524 B2 * | 4/2013 | Aker | A61B 17/1764 606/88 |
| 9,386,994 B2 * | 7/2016 | Agnihotri | A61B 17/155 |
| 9,414,846 B2 | 8/2016 | Gillman et al. | |
| 9,585,725 B2 | 3/2017 | Bonutti | |
| 9,717,510 B2 | 8/2017 | Smith | |
| 9,782,261 B2 | 10/2017 | Collazo et al. | |
| 9,827,115 B2 | 11/2017 | Walker et al. | |
| 9,839,531 B2 | 12/2017 | Netravali et al. | |
| 9,855,106 B2 | 1/2018 | Jaramaz et al. | |
| 9,872,733 B2 | 1/2018 | Shoham et al. | |
| 2003/0153978 A1 | 8/2003 | Whiteside | |
| 2004/0073228 A1 | 4/2004 | Kienzle et al. | |
| 2004/0128026 A1 | 7/2004 | Harris et al. | |
| 2005/0149041 A1 | 7/2005 | McGinley et al. | |
| 2005/0171545 A1 | 8/2005 | Walsh et al. | |
| 2005/0203528 A1 | 9/2005 | Couture et al. | |
| 2005/0234465 A1 | 10/2005 | McCombs et al. | |
| 2006/0030853 A1 | 2/2006 | Haines | |
| 2006/0122617 A1 * | 6/2006 | Lavallee | A61B 17/155 606/87 |
| 2006/0195111 A1 * | 8/2006 | Couture | A61B 17/15 606/86 R |
| 2006/0200163 A1 | 9/2006 | Roger et al. | |
| 2007/0118055 A1 * | 5/2007 | McCombs | A61B 5/4528 600/587 |
| 2007/0239153 A1 | 10/2007 | Hodorek et al. | |
| 2007/0249967 A1 | 10/2007 | Buly et al. | |
| 2008/0154269 A1 * | 6/2008 | Roger | A61B 17/155 606/88 |
| 2008/0306380 A1 | 12/2008 | Parchak et al. | |
| 2009/0082774 A1 | 3/2009 | Oti et al. | |
| 2009/0131941 A1 | 5/2009 | Park et al. | |
| 2009/0287222 A1 | 11/2009 | Lee et al. | |
| 2010/0076563 A1 * | 3/2010 | Otto | A61B 5/103 623/20.14 |
| 2010/0100192 A1 | 4/2010 | Haines et al. | |
| 2010/0191244 A1 * | 7/2010 | White | A61B 17/157 606/88 |
| 2011/0112542 A1 * | 5/2011 | Gross | A61B 17/1764 606/88 |
| 2011/0130761 A1 | 6/2011 | Plaskos et al. | |
| 2011/0245835 A1 * | 10/2011 | Dodds | A61B 17/1764 606/87 |
| 2011/0257653 A1 * | 10/2011 | Hughes | A61B 34/20 606/79 |
| 2012/0078254 A1 * | 3/2012 | Ashby | A61B 17/1764 606/79 |
| 2012/0078263 A1 | 3/2012 | Parisi et al. | |
| 2012/0123422 A1 | 5/2012 | Agnihotri et al. | |
| 2012/0143200 A1 | 6/2012 | Honiball | |
| 2012/0220859 A1 | 8/2012 | Amiot et al. | |
| 2012/0323244 A1 * | 12/2012 | Cheal | A61B 34/10 606/87 |
| 2013/0172905 A1 | 7/2013 | Iorgulescu et al. | |
| 2013/0197552 A1 | 8/2013 | O'Brien, II | |
| 2013/0317523 A1 | 11/2013 | Borus | |
| 2014/0228860 A1 * | 8/2014 | Steines | A61B 34/30 606/130 |
| 2014/0243833 A1 | 8/2014 | Smith | |
| 2014/0257293 A1 | 9/2014 | Axelson, Jr. et al. | |
| 2015/0057758 A1 | 2/2015 | Axelson, Jr. et al. | |
| 2015/0164527 A1 | 6/2015 | Maier et al. | |
| 2016/0030063 A1 | 2/2016 | Pack et al. | |
| 2016/0045268 A1 | 2/2016 | Keppler et al. | |
| 2016/0361072 A1 | 12/2016 | Jaramaz et al. | |
| 2016/0374693 A1 | 12/2016 | Van Citters et al. | |
| 2017/0007331 A1 | 1/2017 | Couture et al. | |
| 2017/0014189 A1 | 1/2017 | Jaramaz et al. | |

FOREIGN PATENT DOCUMENTS

| | | |
|---|---|---|
| WO | 2011106399 A1 | 9/2011 |
| WO | 2013136303 A1 | 9/2013 |
| WO | 2015131133 A1 | 9/2015 |
| WO | 2015131138 A1 | 9/2015 |

OTHER PUBLICATIONS

Chinese Office Action for CN20130058810.6 dated Feb. 6, 2017.
Chinese Office Action for CN201480027135.5 dated Jan. 17, 2017.

(56) References Cited

OTHER PUBLICATIONS

Delp et al. "An Interactive Graphics-Based Model of the Lower Extremity to Study Orthopaedic Surgical Procedures" (Aug. 1990) IEE Transactions on Biomedical Engineering 37(8): 757-767.

DiGioia et al. "HipNav: Pre-operative Planning and Intra-operative Navigational Guidance for Acetabular Implant Placement in Total Hip Replacement Surgery" (Nov. 1995) Preceedings of CAOS '96 1-8.

Dillman et al. "Haptic Devices in Medical s" (Jun. 23, 1999) Institute for Process Control and Robotics, 1st International rkshop, Paris, France, pp. 12-22.

Extended Search Report dated Oct. 16, 2017 for corresponding European Patent Application No. 15754408.1.

Extended Search Report dated Oct. 19, 2017 for corresponding European Patent Application No. 15755754.7.

Freysinger et al. "A Passive-Marker-Based Optical System for Computer-Aided Surgery in Otorhinolaryngology: Development and First Clinical Experiences" (Feb. 2002) The Laryngoscope 112(2):409.

Harris et al. "Experiences with Robotic Systems for Knee Surgery" (Mar. 19-22, 1997) Springer-Verlag, London, UK 757-766.

International Search Report and Written Opinion for PCT/US2015/018155 dated May 27, 2015.

International Search Report and Written Opinion for PCT/US2015/018161 dated May 27, 2015.

O'Toole III et al. "Towards More Capable and Less Invasive Robotic Surgery in Orthopaedics" (1995) Computer Vision, Virtual Reality and Robotics in Medicine 905: 123-130.

Taylor et al. "An Image-Directed Robotic System for Precise Orthopaedic Surgery" (Jun. 1994) IEE Transactions on Robotics and Automation 10 (3): 261-275.

Troccaz et al. "The Use of Localizers, Robots and Synergistic Devices in CAS" (Nov. 21, 2005) First Joint Conference: Computer Vision, Virtual Reality and Robotics in Medical and Medical Robotics and Computer-Assisted Surgery 1205: 725-736.

DiGioia et al. "An Integrated Approach to Medical Robotics and Computer Assisted Surgery in Orthopaedics" (1995) Carnegie Mellon University 106-111.

European Office Action and Written Opinion for EP 15755754.7 dated Sep. 27, 2019.

\* cited by examiner

SYSTEM AND METHODS FOR POSITIONING BONE CUT GUIDE

CLAIM OF PRIORITY

This patent application is a divisional of U.S. patent application Ser. No. 14/634,363, titled "System and Methods for Positioning Bone Cut Guide," filed on Feb. 27, 2015, which is hereby incorporated by reference in its entirety and which claims the benefit of priority of U.S. Provisional Patent Application No. 61/946,428, titled "System and Methods for Positioning Bone Cut Guide," filed on Feb. 28, 2014, which is hereby incorporated by reference herein in its entirety.

TECHNICAL FIELD

This document relates generally to computer-aided orthopedic surgery, and more specifically to systems and methods for positioning a cut guide to a target bone and for altering the target bone using the cut guide.

BACKGROUND

The use of computers, robotics, and imaging to aid orthopedic surgery is well known in the art. There has been a great deal of study and development of computer-aided navigation and robotics systems used to guide surgical procedures. For example, a precision freehand sculptor (PFS) employs a robotic surgery system to assist the surgeon in accurately cutting a bone into a desired shape. In interventions such as total hip replacement, computer-aided surgery techniques have been used to improve the accuracy, reliability of the surgery. Orthopedic surgery guided by images has also been found useful in preplanning and guiding the correct anatomical position of displaced bone fragments in fractures, allowing a good fixation by osteosynthesis.

A cut guide can be used in an orthopedic surgery to assist a surgeon in cutting or modifying some portions of a target bone. For example, in joint replacement surgeries such as total hip replacement (THR) or total knee replacement (TKR), a cut guide can be temporarily attached to the target bone such as a femur or a tibia. An orthopedic surgical cutting tool can be used together with the cut guide to allow the surgeon to selectively cut portions of the ends of the target bone and replaced with endoprosthetic implants. Positioning a cut guide for use in preparing the target bone can be a time consuming and complicated process, which is critical to positive outcomes for the patient.

SUMMARY

Quick and reliable positioning of a cut guide can be crucial to the outcome of orthopedic surgeries such as prosthesis implantation. In joint replacement surgeries, for example, portions of the articulation tissues of a target bone, such as acetabulum, a femur, or a tibia, need to resected and altered to allow an implant to be securely positioned onto the target bone. A cut guide positioned on the target bone can be used to guide a cutting saw to resect the target bone to a desired shape. Proper positioning of the cut guide on the bone can improve the accuracy of the bone resection and reduce procedure time. On the contrary, improper positioning of the cut guide can result in undesirable cutting surfaces on the target bone, which can further cause impingement, increased rates of implant dislocation, wear and failure of the implant, among many other complications. The procedure time can also be lengthened due to the requirement of modifying the undesirable cutting shape.

Positioning of cut guide onto a target bone usually requires a surgeon to mentally map and compare the shape, orientation, and relative positions of the implant and the target bones. Mechanical jigs that align to general specifications, rather than aligning to parameters optimal for the patient. This method can be difficult to operate and may suffer from lack of reliability and certainty. Determining and visualizing the correct positions and orientations of the prosthesis with respect to the target bone can be practically difficult. Computer-aided tools can be used to assist the surgeon in positioning the cut guide relative to the bone. However, often the computer-assistance is limited to intraoperative navigation of traditional cutting jigs. The designs of these jigs, the tools to align them, and the implants that they support are all compromises meant to serve a general population. Other systems uses computers to analyze patient specific images used to design patient-conforming instrumentation and sometimes even implants specific to the patient. However, these images either use ionizing radiation (e.g. computed tomography images) or are prone to error or gaps in tissue differentiation (e.g. magnetic resonance imaging).Therefore, the present inventors have recognized that there remains a considerable need for systems and methods that can assist the surgeon in reliably positioning a cut guide onto the target bone with improved accuracy, speed, and consistency, while still allowing for some customization.

Various embodiments described herein can help improve the efficacy and the reliability in positioning a cut guide onto a target bone to alter a portion of the target bone. For example, an orthopedic surgical device can comprise a cut guide that is configured to be adjustably positioned onto or otherwise conform to the target bone. The cut guide includes a plurality of landing members. Each landing member includes a coupling feature that can removably couple to a landing site of the target bone. The cut guide also includes one or more guide members on the guide body. Each guide member can be sized, shaped or configured to constrain and guide a cutting tool along a respective cutting trajectory. The guide member can guide the cutting tool to cut the target bone along the respective cutting trajectory when the landing members are coupled to the landing site of the target bone. In an example, the guide member can include guide slots or surfaces for guiding a surgical saw in making cuts on a target bone. Multiple cut guides with the same cutting trajectories can be made available that have different landing member placements, in order to accommodate different sizes and shapes of bones.

A system embodiment for use in an orthopedic surgery on a target bone can comprise a cut guide adjustably positionable onto a target bone via two or more coupling receptacles created on the target bone. The cut guide can include one or more guide members and a plurality of landing members. The system also includes an input interface that can receive a target bone representation, and a model receiver module that can receive a generic post-coupling bone model. The target bone representation can include a data set representing two or more landing sites of the target bone, and the generic post-coupling bone model can include a data set representing a bone having two or more coupling receptacles each sized, shaped or otherwise configured to receive and secure the respective coupling feature of the landing members. The system can include a navigation-based guide coupling preparation system that can generate a plan for positioning the cut guide onto or conforming to the target bone. The system can further include a display module that provides presentations of the coupling between the target bone and the cut guide.

A method embodiment for operating a system for use in an orthopedic surgery on a bone can comprise the operations of providing a cut guide that is adjustably positionable onto or conformed to the target bone, and receiving a target bone representation and a generic post-coupling bone model. The target bone representation can include a data set representing two or more landing sites of the target bone, and the generic post-coupling bone model can include a data set representing a bone having two or more coupling receptacles configured to receive and secure the respective coupling feature of the landing members. The method can comprise the operations of generating a cut guide positioning plan for positioning the cut guide onto or conforming to the target bone, producing at the landing sites coupling receptacles that are sized, shaped or configured to receive and secure the respective coupling features of the landing members, and attaching the cut guide to the landing site of the target bone by engaging the coupling features with the coupling receptacles.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices and methods for positioning a cut guide onto a target bone using a plurality of coupling receptacles produced with the assistance of a navigation-based guide coupling preparation system. Various embodiments described herein can help improve the efficacy and the reliability in osteoplasty planning, such as resecting portions of bone surface for cut guide positioning. The methods and devices described herein can also be applicable to planning surgery of pathological bones under various other conditions.

Figure 1B:
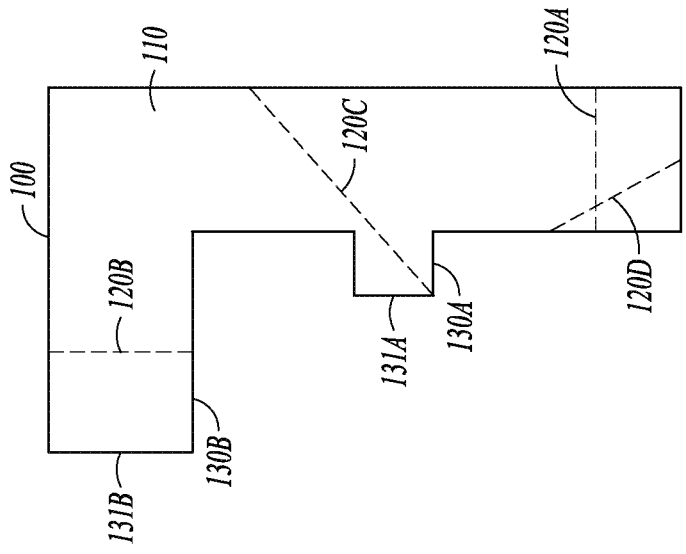
FIGS. 1A-D illustrate an example of an orthopedic surgical device for use in operating on a target bone.
Figure 1A:
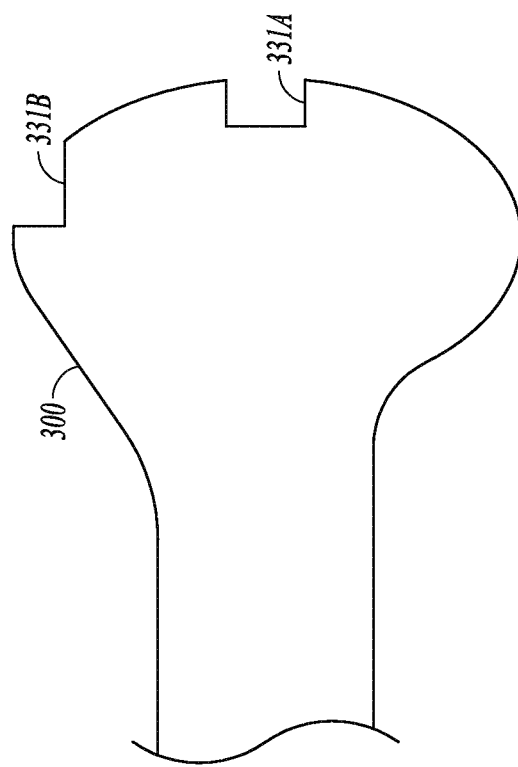

FIGS. 1A-D illustrate an example of an orthopedic surgical device for use in operating on a target bone 300. The orthopedic surgical device comprises a cut guide 100, illustrated in FIG. 1B, configured to be adjustably positioned onto or otherwise conform to the target bone 300 as illustrated in FIG. 1A. The cut guide 100 includes a guide body 110 forming the cut guide 100, and a plurality of landing members such as 130A-B. The guide body 110 forms the supporting structure of the cut guide 100, and can be made of metal, alloy, polymer, or other rigid dimensionally stable materials.

The guide body 110 includes one or more guide members 120A-D. Each guide member can be sized, shaped or otherwise configured to constrain and guide a cutting tool (not shown) along a respective cutting trajectory determined by the guide member. The guide members 120A-D can have slotted structures sized to securely receive and constrain the cutting tool, and allow the cutting tool to move freely within the respective slotted structure. The guide members 120A-D can have openings on an exterior of the guide body 110. The openings can be sized to facilitate placement of the cutting tool into one or more of the guide members 120A-D, and connection between a portion of the cutting tool and an external driving device such as a robotic arm for manipulating the cutting tool within the guide members.

Each guide member (such as a slot) has a pre-determined orientation that defines the cutting trajectory. As illustrated in FIG. 1B, the guide member 120A is horizontally oriented, the guide member 120B vertically oriented, and the guide members 120C and 120D each oriented at specified tilt angles. The orientations of the guide members 120A-D can be different from each other, thereby allowing bone cuts from different angles. In some examples, at least two guide members have the same orientation. This provides a system end-user with flexibility in selecting desired amount of bone cut along a particular cutting plane. The number of guide members on the guide body 110 can be more than what is needed for resecting a particular target bone. Such redundancy of guide members can make the cut guide 100 a generic tool for modifying target bones that have different desired post-operative sizes or shapes.

Each of the landing members 130A-B on the cut guide 100 can include a respective coupling feature. The coupling features can be configured to removably couple to the target bone 300 at two or more landing sites on the target bone 300. The landing sites define desired locations on the target bone onto which the cut guide can be securely positioned.

As illustrated in FIG. 1B, on the cut guide 100, the coupling features can further include protruding portions such as 131A-B extended from the landing members 130A-B. The protruding portions 131A-B can have a shape of a cylinder, a cube, a rectangular prism, a triangular prism, a pyramid, a cone, or other three-dimensional structures. As illustrated in FIG. 1A, on the target bone 300, two or more coupling receptacles such as 331A-B can be produced at the landing sites with assistance of a navigation-based guide coupling preparation system. The coupling receptacles 331A-B on the target bone 300 each include a recessed portion that is sized, shaped or otherwise configured to receive and secure a respective protruding portion, such as 131A-B, of the coupling features on the cutting guide 100. For example, when the protruding portion 131A is in a shape of rectangular prism, the corresponding coupling receptacle 331A can be a receptacle in a shape of rectangular prism sized to securely match the protruding portion 131A. The interfacing surfaces of the protruding portion 131A and of the coupling receptacle 331A can be processed to allow for an interference fit in at least one dimension, such that the protruding portion 131A can be held within the coupling receptacle 331A by compression or by friction. The amount of interference can be produced at either or both of the interfacing surfaces of the protruding portion 131A and of the coupling receptacle 331A so as to achieve desired tightness of fit.

In some examples, the size and shape of the coupling receptacle can also be determined using the information including the location of the landing site of the target bone, and the anatomical, mechanical, or physical properties of the bone and surrounding tissues at the landing site. The coupling between the cut guide 100 and the target bone 300 can therefore be accomplished by engaging the protruding portions 131A-B into the respective coupling receptacles 331A-B on the target bone 300. Examples of creating the coupling receptacles 331A-B for positioning the cut guide 100 onto the target bone 300 are discussed below, such as with reference of FIG. 3.

The landing members 131A-B can be an extended portion of the guide body 100. In some examples, the landing members 131A-B can be structures separate from but fixed onto an exterior of the guide body 100. In an embodiment, at least one of the landing members is reconfigurable. The reconfigurable landing member can be connected to the guide body 100 via an adjustable connector, through which the reconfigurable landing member can have at least one degree of freedom of movement relative to the guide body 100. Examples of the adjustable connector can include a releasable lock, such that the reconfigurable landing member can be adjustably locked onto the guide body 110 when the reconfigurable landing member is positioned once the cutting guide is at the landing site and attached to the target bone, or when the reconfigurable landing member is not used for attaching to the target bone.

Figure 1D:
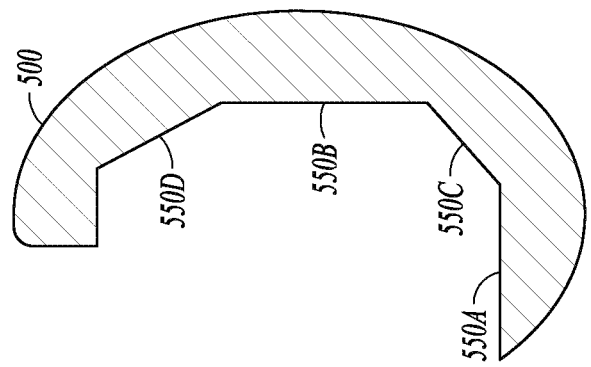
Figure 1C:
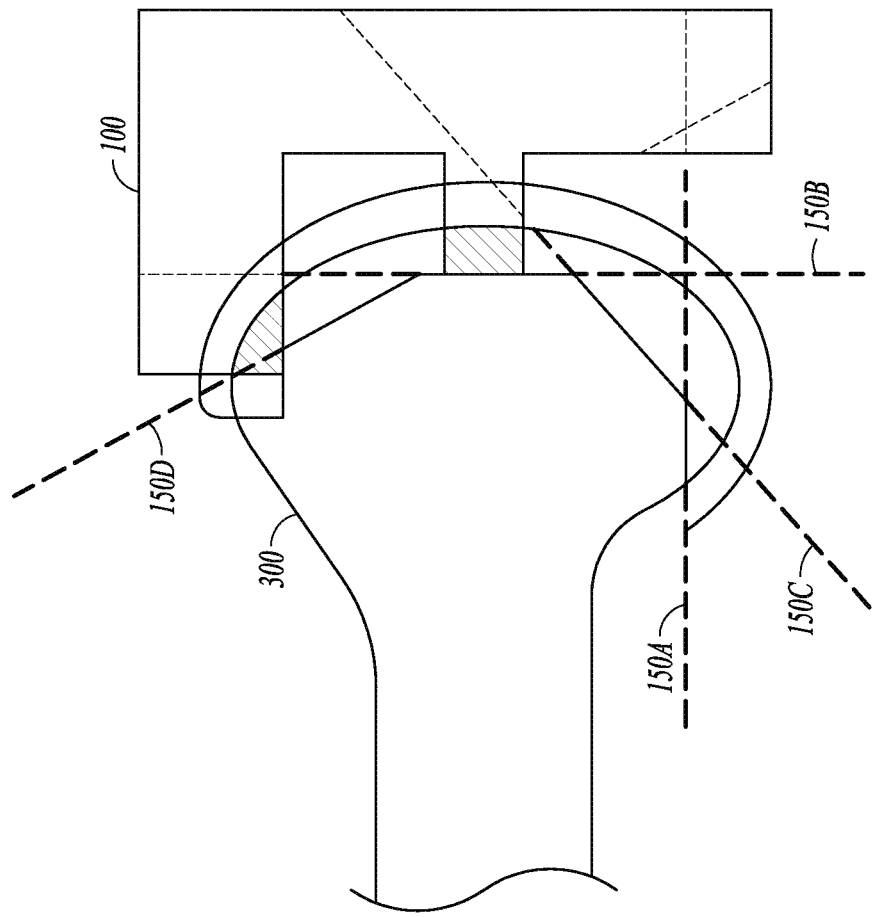

FIG. 1C illustrates an example of positioning the cut guide 100 onto the target bone 300 such as via coupling between the protruding portion 131A-B and the coupling receptacles 331A-B. The guide members 120A-D can guide a cutting tool (not shown) to cut the target bone 300 along the cutting trajectories 150A-D as defined by the orientations of the guide members 120A-D. In some examples, the protruding portions 131A-B of the landing members do not cross the cutting trajectories or the cutting planes 150A-D. This will prevent bone cutting along the cutting trajectories from interfering with the protruding portion 131A-B that are coupled to the coupling receptacles 331A-B. When the bone cut is completed, an implant 500 can be attached to the post-operative bone. As illustrated in FIG. 1D, the implant 500 can include an interfacing surface sized and shaped to be in close contact with the post-operative surfaces of the target bone. The interfacing surface can include multiple facets 550A-D oriented in conformity with the cutting planes 150A-D, respectively.

Figure 2A:
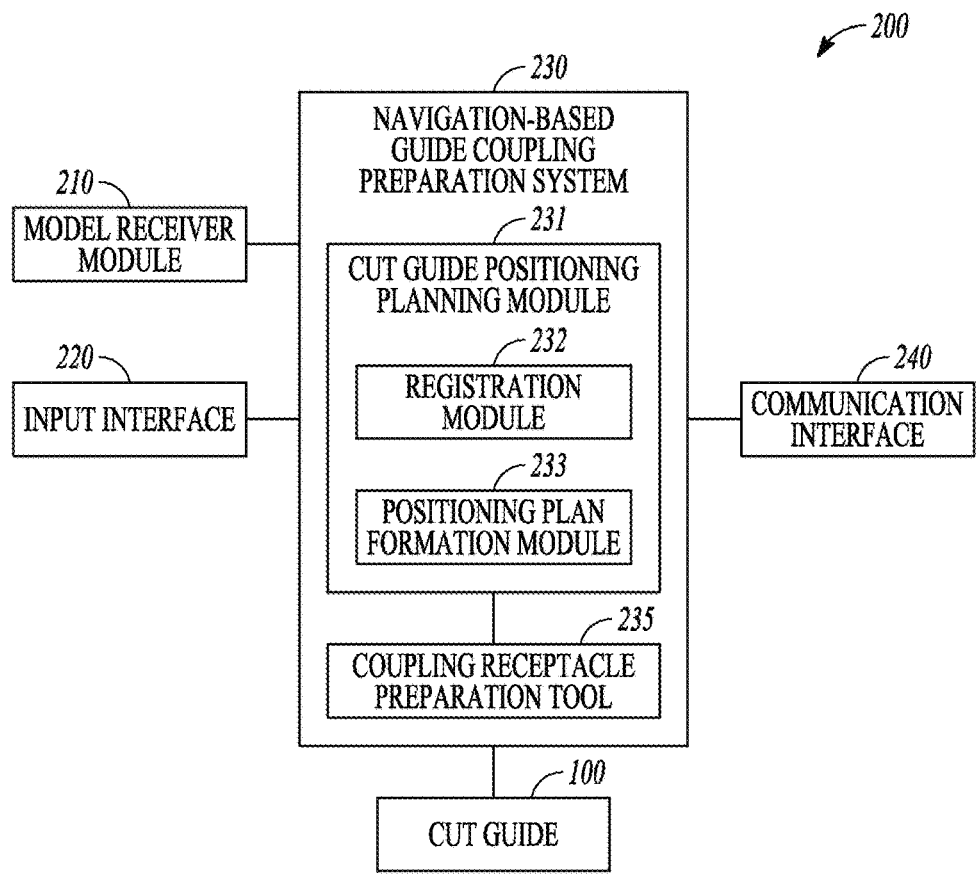
FIGS. 2A-B are block diagrams that illustrate an example of a cut guide positioning system.
Figure 2B:
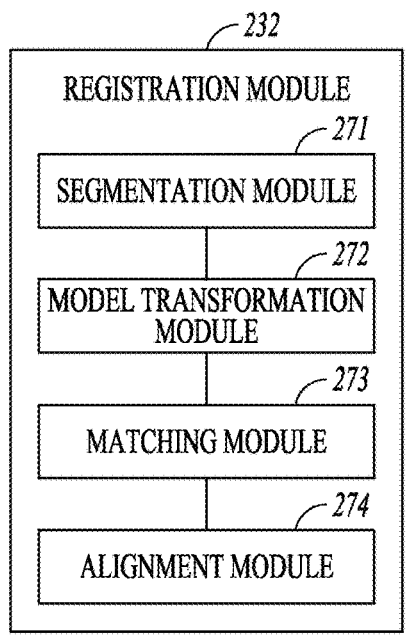

FIGS. 2A-B are block diagrams that illustrate an example of a cut guide positioning system 200 for use in an orthopedic surgery. The system 200 includes a cut guide 100, a model receiver module 210, an input interface 220, a navigation-based guide coupling preparation system 230, and a communication interface 240. The system 200 can be configured to securely position the cut guide 100 onto a target bone via two or more coupling receptacles created on the target bone. Once positioned on the target bone, the cut guide 100 can be used to guide resection of a portion of the target bone for prosthesis implantation.

The model receiver module 210 can be configured to receive a generic post-coupling bone model ($M_{coupling}$). The model $M_{coupling}$ can include a data set representing a bone having an anatomical origin comparable to the target bone to be altered by the system 200. The data set can include shape or appearance information of the bone. The model $M_{coupling}$ can be in a form of a parametric model, a statistical model, a shape-based model such as a statistical shape model, or a volumetric model. The model $M_{coupling}$ can also be based on physical properties of the normal bone, such as an elastic model, a geometric spine model, or a finite element model.

The model $M_{coupling}$ can include representations of two or more coupling receptacles each sized, shaped or otherwise configured to receive and secure the respective coupling feature on the cut guide 100, such as protruding portions 131A-B. The coupling receptacle representation can include indications of locations, sizes, shapes, volume, or other geometric or morphological descriptors. In an example, the model $M_{coupling}$ can be derived from a plurality of images of post-coupling bones (i.e., bones with the coupling receptacles created) having comparable anatomical origin from a group of subjects. In another example, the coupling receptacle representation includes computer-simulated graphs or annotative markings that identify the boundaries of the recessed portions of the coupling receptacle. The sizes, shapes, volume, or other geometric or morphological descriptors of the coupling receptacle representations can be determined using the size, shape, volume, or other geometric or morphological descriptors of the respective protruding portion (such as 131A-B) of the landing members on the cut guide 100. The computer-simulated coupling receptacle representation can be separately generated and then added to a coupler-free normal bone model to create the generic post-coupling bone model $M_{coupling}$.

The model $M_{coupling}$ can be generated using a system external to the system 200, and stored in a machine-readable medium such as a memory device. The model receiver module 210 can retrieve model $M_{coupling}$ from the memory device upon receiving a command from an end-user. Alternatively, the system 200 can include a post-coupling bone model generator that can create a generic post-coupling bone model ($M_{coupling}$) using shape data or appearance data. The shape data may include geometric characteristics of a bone such as landmarks, surfaces, boundaries of three-dimensional images objections. The appearance data may include both geometric characteristics and intensity information of a bone. The shape or appearance data can be constructed from a plurality of medical images of the normal bones of comparable anatomical origin from a group of subjects. The medical images can include two-dimensional (2D) or three-dimensional (3D) images, including an X-ray, an ultrasound image, a computed tomography (CT) scan, a magnetic resonance (MR) image, a positron emission tomography (PET) image, or a single-photon emission computed tomography (SPECT) image, or an arthrogram. The shape or appearance data can be constructed from a plurality of point clouds acquired from bones having comparable anatomical origin from a group of subjects using a coordinated measuring system such as one or more tracking probes.

The input interface 220 can be configured to receive a target bone representation ($X_{pre-coupling}$) from a patient database. Alternatively, the target bone representation ($X_{pre-coupling}$) can be generated by an imaging system or other image acquisition module within or external to the system 200, and received by the system 200 via the input interface 220. Examples of target bone can include an acetabulum, a proximal or distal extremity of a femur, a proximal or distal extremity of a tibia, or other bones in a body. The representation $X_{pre-coupling}$ can be in a form of a medical image, a point cloud, a parametric model, or other morphological description of the target bone. The representation $X_{pre-coupling}$ includes a data set representing the shape, appearance, or other morphological characteristics of the target bone. The representation $X_{pre-coupling}$ includes two or more landing site representations on a surface of the target bone where two or more coupling receptacles can be created.

The navigation-based guide coupling preparation system 230 can include a cut guide positioning planning module 231 configured to generate a plan for positioning the cut guide onto or conforming to the target bone. The cut guide positioning planning module 231 can include a registration module 232 and a positioning plan formation module 233.

The registration module 232 can take as an input the generic post-coupling bone model $M_{coupling}$ and the target bone representation $X_{pre-coupling}$, register $M_{coupling}$ to $X_{pre-coupling}$, and create a registered post-coupling bone model $M^*_{coupling}$. FIG. 2B is a block diagram illustrating an embodiment of the registration module 232. In this embodiment, the registration module 232 can include a segmentation module 271, a model transformation module 272, a matching module 273, and an alignment module 274. The segmentation module 271 can be configured to partition the model $M_{coupling}$ and the target bone representation $X_{pre-coupling}$ each into a plurality of segments. Each segment can represent a specified anatomical structure. In some examples, a label can be assigned to each of the segments, such that the segments with the same label share specified characteristics such as a shape, anatomical structure, or intensity. For example, the segmentation module 271 can differentiate a portion of $M_{coupling}$ containing the coupling receptacle representation from a different portion of the $M_{coupling}$ free of coupling receptacle representation, and identify from the segments of the $M_{coupling}$ a registration area free of coupling receptacles.

The model transformation module 272 can transform the generic post-coupling bone model $M_{coupling}$ to create the registered post-coupling model $M^*_{coupling}$ using a comparison between the coupler-free segment of $M_{coupling}$ and the corresponding segments of the $X_{pre-coupling}$. The transformation can include linear or nonlinear operations such as scaling, rotation, translation, expansion, dilation, or other affine transformation. The transformation can include rigid transformations that preserve the distance (such as translation, rotation, and reflection) or non-rigid transformations such as stretching, shrinking, or model-based transformations such as radial basis functions, splines, or finite element model. In some embodiments, the registration module 232 can employ both the rigid transformation to bring the $M_{coupling}$ in global alignment with the size and orientation of the target bone representation $X_{pre-coupling}$, and the non-rigid transformation to reduce the local geometric discrepancies by aligning the $M_{coupling}$ with the $X_{pre-coupling}$. In some embodiments, the model transformation module 272 can determine a desired transformation $\Theta$ that minimizes the difference between the identified coupler-free segments on the $M_{coupling}$ and the corresponding segments of $X_{pre-coupling}$. The desired transformation $\Theta_{opt}$ can then be applied to the $M_{coupling}$ to create the registered post-coupling model $M^*_{coupling}=\Theta_{opt}(M_{coupling})$. The model $M^*_{coupling}$ contains desired size, shape, volume, and other geometric or morphological descriptors of the coupling receptacles on the target bone.

The matching module 273 can match one or more segments of the registered post-coupling model $M^*_{coupling}$ to the corresponding registration area of the $X_{pre-coupling}$. The alignment module 274 can align the remaining segments of $M^*_{coupling}$ with the remaining segments of the target bone representation $X_{pre-coupling}$ based at least on the matching. This produces an alignment between the registered post-coupling model $M^*_{coupling}$ and the target bone representation $X_{pre-coupling}$.

Referring back to FIG. 2A, the positioning plan formation module 233 can use the comparison between the registered post-coupling model $M^*_{coupling}$ and the target bone representation $X_{pre-coupling}$ to determine the two or more landing sites on the target bone for respectively creating the coupling receptacles, and determining sizes, shapes, volume, or other geometric or morphological descriptors of the coupling receptacles. The comparison can be performed on all or selected segments (such as the segments containing the coupling receptacles) of the registered post-coupling model $M^*_{coupling}$ and the target bone representation $X_{pre-coupling}$.

As illustrated in FIG. 2A, the system 230 can further include a coupling receptacle preparation tool 235. The coupling receptacle preparation tool 235 can be a temporary tool used for producing the two or more coupling receptacles on the landing site of the target bone according to the positioning plan generated by the positioning plan formation module 233. The coupling receptacle preparation tool 235 can be operated manually by an end-user, or automatically by a computer-controlled system. An example of such a cutting tool can be found in Brisson et al., U.S. Pat. No. 6,757,582, entitled "Methods and systems to control a shaping tool", which is incorporated herein by reference in its entirety. Examples of the coupling receptacle preparation tool and the creation of the coupling receptacles are discussed below, such as with reference of FIG. 3.

In some examples, the coupling receptacle preparation tool 235 is operated to progressively create the coupling receptacles using a comparison between the registered post-coupling model $M^*_{coupling}$ and a perioperative target bone representation $X_{peri-coupling}$. The input interface 220 can receive the perioperative target bone representation $X_{peri-coupling}$ including coupling receptacle representations during the process of creating the coupling receptacles. The perioperative representation $X_{peri-coupling}$ can be updated in real-time such as using a camera and a monitoring device, or upon receiving a user command. The cut guide positioning planning module 231 can compute a similarity metric between the desired coupling receptacles on the registered post-coupling model $M^*_{coupling}$ and the corresponding perioperative coupling receptacles on the perioperative target bone representation $X_{peri-coupling}$. Examples of the similarity metric can include L1 norm, L2 norm (Euclidian distance), infinite norm, or other norm in the normed vector space. The similarity metric can also include correlation coefficient, mutual information, or ratio image uniformity. If the similarity metric meets a specified criterion such as falling within a specified range or below a threshold value, the perioperative coupling receptacles on the representation $X_{peri-coupling}$ are deemed substantially similar to the desired coupling receptacle on the registered post-coupling model $M^*_{coupling}$, and the positioning plan formation module 233 can generate an indicator indicating the completion of the coupling receptacle preparation.

The communication interface 240, coupled to the navigation-based guide coupling preparation system 230, can be configured to present information of the model and the target bone in audio, visual, or other multi-media formats to assist the surgeon during the process of creating and evaluating a surgical plan. The information presented can include the generic post-coupling bone model $M_{coupling}$, the registered post-coupling model $M^*_{coupling}$, the target bone representation $X_{pre-coupling}$, the landing sites representation and the coupling receptacles on the target bone, the perioperative target bone representation $X_{peri-coupling}$, the similarity metric between the desired coupling receptacles and the perioperative coupling receptacles, and the indication of the completion of the coupling receptacle preparation. In an example, the communication interface 240 can include a display module such as a monitor for displaying dialog, text, 2D or 3D graphs, or animations of the bone models and the target bone representation, among other things. The graphs or animation can include color-codes, annotations, or other visual enhancements on the perioperative coupling receptacles. The communication interface 240 can also include a user input device configured to receive user input to accept or modify the surgical plan generated by the surgical planning module 130.

The communication interface 240 can communicate over an internal bus to other modules within the system 200. In some examples, the communication interface 240 can be configured to communicate with one or more external devices including, for example, a tracking device, a positioning device, a surgical navigation system, or a medical robotic system. The communication interface 240 can include both wired interface (such as cables coupled to the communication ports on the communication interface 240) and wireless connections such as Ethernet, IEEE 802.11 wireless, or Bluetooth, among others.

Figure 3B:
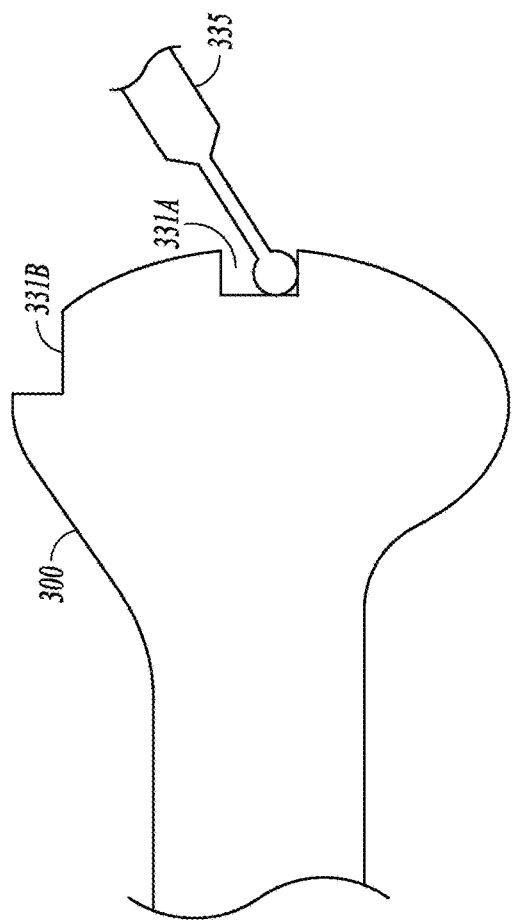
FIGS. 3A-B illustrate an example of preparing coupling receptacles on a target bone.
Figure 3A:
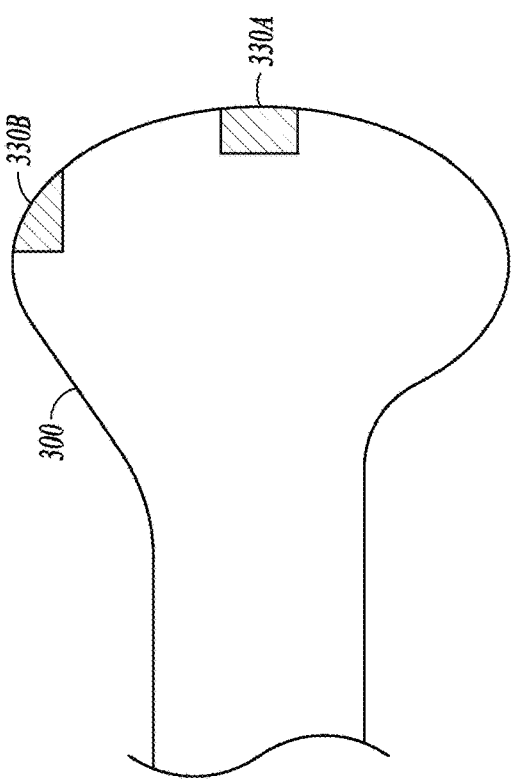

FIGS. 3A-B illustrate an example of preparing coupling receptacles on a target bone 300. In this example, two coupling receptacles 331A-B are created at two different landing sites 330A-B on the surface of the target bone 300. The coupling receptacles can be created using a temporary coupling receptacle preparation tool 335, or any suitable surgical cutting tool, according to a positioning plan such as generated by the cut guide positioning planning module 231. The coupling receptacles 331A-B can each include a respective recessed portion sized, shaped or otherwise configured to receive and secure a protruding portion of the coupling feature on the landing members of a cut guide 100, such as the protruding portions 131A-B. The landing sites 330A-B, as well as the sizes, shapes, volume, or other geometric or morphological descriptors of the coupling receptacles, can be determined by the cut guide positioning planning module 231. In an example, the size and shape of the coupling receptacles can be determined based on the size and shape of the protruding portions 131A-B of the landing members. The recessed portion of the coupling receptacles 331A-B can be in a shape of a cylinder, a cube, a rectangular prism, a triangular prism, a pyramid, a cone, or other three-dimensional shapes. The size and shape of the coupling receptacles can also be determined based on the location of the landing sites, or based on the anatomical, mechanical, and physical properties of the bone and soft tissues at the landing sites.

The temporary coupling receptacle preparation tool 335 can be an embodiment of the coupling receptacle preparation tool 235. In an example where the coupling receptacles include recessed portions such as 331A-B for receiving and securing the protruding portions of the landing members, the coupling receptacle preparation tool 335 can include a surgical drill, a surgical mill, a surgical saw, or other surgical equipment capable of creating the recessed portion on the target bone. The temporary coupling receptacle preparation tool 335 can be operated manually by an operator such as a surgeon. Alternatively, it can be connected to and operated by an automated computer-controlled system such as a precision freehand sculptor (PFS) or other robotic surgical system.

Figure 4A:
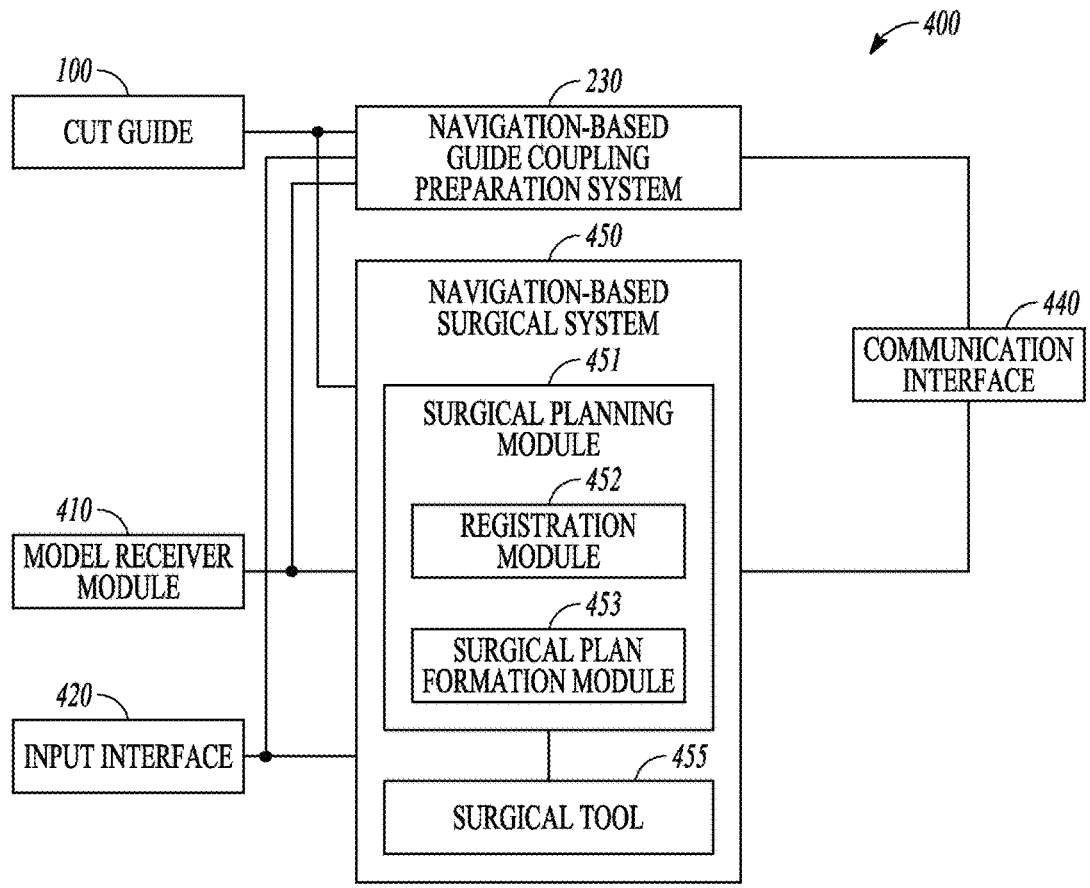
FIGS. 4A-B are block diagrams that illustrate an example of an orthopedic surgical system.
Figure 4B:
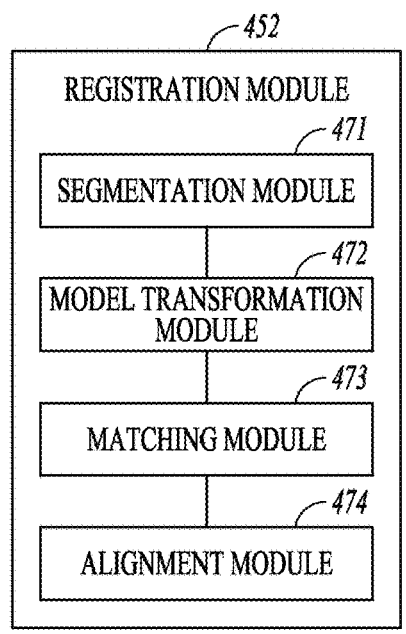

FIGS. 4A-B are block diagrams that illustrate an example of an orthopedic surgical system 400 for operating on a target bone. The system 400 includes a cut guide 100, a model receiver module 410, an input interface 420, a navigation-based guide coupling preparation system 230, a navigation-based surgical system 450, and a communication interface 440. The system 400 includes some or all components of the system 200, and thus can be configured to position the cut guide 100 onto a target bone via two or more coupling receptacles created on the target bone. Additionally, the system 400 can be configured to assist in bone cut after the cut guide is positioned onto or otherwise conforms to the target bone.

The model receiver module 410 can be an embodiment of the model receiver 210, and can receive a generic post-coupling bone model ($M_{coupling}$). Additionally, the model receiver module 410 can be further configured to receive a generic post-operative bone model ($M_{post-op}$) including a data set representing a shape or appearance of a post-operative bone (i.e., after the bone cut). The model $M_{post-op}$ can be in a form of a parametric model, a statistical model, a shape-based such as a statistical shape model, or a volumetric model. The model $M_{post-op}$ can be derived from a plurality of images of post-operative bones having comparable anatomical origin from a group of subjects. Alternatively, at least a portion of the model $M_{post-op}$, such as resected surfaces that interface with the implant 500, can be computer-simulated representation of the post-operative bone surface. The post-operative bone model $M_{post-op}$ can be generated using an external system and retrieved from a database, or it can be generated by a system within or external to the system 400.

The input interface 420 can be an embodiment of the input interface 220, and can receive a target bone representation ($X_{pre-coupling}$) including a data set representing the shape, appearance, or other morphological characteristics of the target bone including representations of the two or more landing sites on the target bone. Additionally, the input interface 420 can be further configured to receive a preoperative target bone representation including a data set representing a portion of the target bone to be altered ($X_{pre-op}$), which can be different and broader than the landing sites on the target bone. A set of bone cuts on the target bone can be determined by the navigation-based surgical system 450. The representation $X_{pre-op}$ can include one of more of a medical image, a point cloud, a parametric model, or other morphological description of the target bone. In some examples, the input interface 420 can be configured to be coupled to an imaging system or other image acquisition module within or external to the system 400. The post-operative bone model $M_{post-op}$ can have data format or modality comparable to the target bone representation $X_{pre-op}$.

In some embodiments, the representation $X_{pre-op}$ can be taken as the post-coupling representation of the target bone, that is, the target bone presentation $X_{pre-coupling}$ with two or more coupling receptacles created according to the navigation-based guide coupling preparation system 230. The representation $X_{pre-op}$ thus includes both a data set representing a portion of the target bone to be altered as well as the coupling receptacle representations.

The navigation-based surgical system 450 can include a surgical planning module 451 configured to generate a surgical plan for altering at least a portion of the target bone when the cut guide is securely positioned onto or otherwise conforms to the target bone. Similar to the cut guide positioning planning module 231, the surgical planning module 451 can include a registration module 452 and a surgical plan formation module 453.

The registration module 452 can be configured to register $M_{post-op}$ to $X_{pre-op}$ and create a registered post-operative bone model $M^*_{post-op}$. FIG. 4B is a block diagram illustrating an embodiment of the registration module 452. Similar to the registration module 232 in FIG. 2B, the registration module 452 in this embodiment includes a segmentation module 471, a model transformation module 472, a matching module 473, and an alignment module 474. The segmentation module 471 can partition the bone model $M_{post-op}$ and the pre-operative bone representation $X_{pre-op}$ each into a plurality of segments. Each segment can represent a specified anatomical structure. In some examples, a label can be assigned to each of the segments, such that the segments with the same label share specified characteristics such as a shape, anatomical structure, or intensity. For example, the segmentation module 471 can differentiate a portion of the $M_{post-op}$ containing the resection surface representation from a different portion of the $M_{post-op}$ free of resection surface representation, and identify from the segments of the $M_{post-op}$ a registration area free of resection surface representation.

The model transformation module 472 can transform the generic post-coupling bone model $M_{post-op}$ to create a registered post-operative bone model $M^*_{post-op}$ such as using a comparison between the segment of the $M_{post-op}$ free of resection surface representation and the corresponding segments of the $X_{pre-op}$. The transformation can include linear or nonlinear operations, rigid or non-rigid transformations as discussed with reference to FIG. 2B. The model transformation module 472 can determine a desired transformation that minimizes the difference between the identified coupling receptacle-free segments on the $M_{post-op}$ and the corresponding segments of $X_{pre-op}$. The desired transformation $\Psi_{opt}$ can then be applied to the $M_{post-op}$ to create the registered post-operative model $M^*_{post-op}=\Psi_{opt}(M_{post-op})$. The model $M^*_{post-op}$ contains desired size, shape, volume, and other geometric or morphological descriptors of the bone cuts on the target bone.

The matching module 473 can match one or more segments of the registered post-operative model $M^*_{post-op}$ to the corresponding registration area of the $X_{pre-op}$, and align the remaining segments of $M^*_{post-op}$ with the remaining segments $X_{pre-op}$ based at least in part on the matching. This produces an alignment between the registered post-operative model $M^*_{post-op}$ and the target bone representation $X_{pre-op}$.

The surgical plan formation module 453 can be configured, using the registered post-operative model $M^*_{post-op}$, to generate a surgical plan for cutting the target bone such that the altered target bone is in substantial conformity to the registered post-operative model $M^*_{post-op}$. The surgical plan formation module 453 can include a guide member selection module to select one or more guide members from those available (such as 102A-D) on the cut guide 100. In an embodiment, the guide member selection module can compare the orientations of the desired bone cuts as defined by the registered post-operative model $M^*_{post-op}$ to the cutting trajectories of the available guide members in the cut guide 100, and select the guide members that match the orientation of the desired bone cuts.

The surgical plan formation module 453 can also include a cutting sequence scheduler module to determine an ordered sequence of executing bone cuts along the cutting trajectories (such as 150A-D) associated with the selected guide members. The cutting sequence can be determined using the anatomical, geometric, physical and mechanical properties of the portions of the bone to be altered. The cutting sequence can also be scheduled considering the locations, sizes, shapes, volumes, or other geometric or morphological descriptors of the coupling receptacles relative to the cutting trajectories. For example, the bone cuts along the cutting trajectories that are spatially farther away from the coupling receptacles can be executed earlier (i.e., at the front of the sequence), the bone cuts along the cutting trajectories that are spatially closer to the coupling receptacles can be executed later (i.e., at a latter part of the sequence), and the bone cuts along the cutting trajectories that intersect with one or more coupling receptacles can be executed last (i.e., at the end of the sequence). The ordered bone cuts as such allow the cut guide to remain securely attached to the target bone while performing bone cuts, and prevent a bone cut from interfering with the coupling between the cut guide and the target bone. Examples of selecting guide members and generating an ordered bone cut sequence are discussed below, such as with reference of FIGS. 5A-C.

As illustrated in FIG. 4A, the navigation-based surgical system 450 can further include a surgical tool 455 for resecting the target bone according to the surgical plan such as generated by the surgical planning module 451. The surgical tool 455 can be adjustably positioned within the guide members, and can securely move along the cutting trajectories defined by the guide members. Examples of the surgical too can include a surgical saw, a surgical blade, a surgical saw-blade, a surgical mill, or other surgical equipment. The surgical tool 455 can be operated manually by an end-user such as a surgeon. Alternatively, the surgical tool 455 can be connected to and operated by an automated computer-controlled system such as a precision freehand sculptor (PFS) or other robotic surgical.

In some examples, perioperative target bone representation during the bone cuts can be updated in real-time such as using a camera and a monitoring device, or upon receiving a user command. The surgical planning module 451 can compute a similarity metric between the desired bone cuts on $M^*_{post-op}$ and the perioperative bone cuts, and determines the bone cuts on the target bone are completed if the similarity metric meets a specified criterion such as falling within a specified range or below a threshold value. The surgical plan formation module 453 can generate an indicator indicating the completion of the bone cut.

The communication interface 440 can be an embodiment of the communication interface 240, and can generate and display on a display module one or more of the generic post-coupling bone model ($M_{coupling}$) and the target bone representations ($X_{pre-coupling}$), among other information as discussed with reference to FIG. 2A. Additionally, the communication interface 440 can further be configured to generate and display on the display module one or more of the data set representing the portion of the target bone to be altered ($X_{pre-op}$), the generic post-operative bone model ($M_{post-op}$), the selected guide members on the cut guide, the scheduled sequence of bone cuts along the cutting trajectories, the perioperative target bone representation during bone cutting, and the indication of the completion of bone cuts.

Figure 5A:
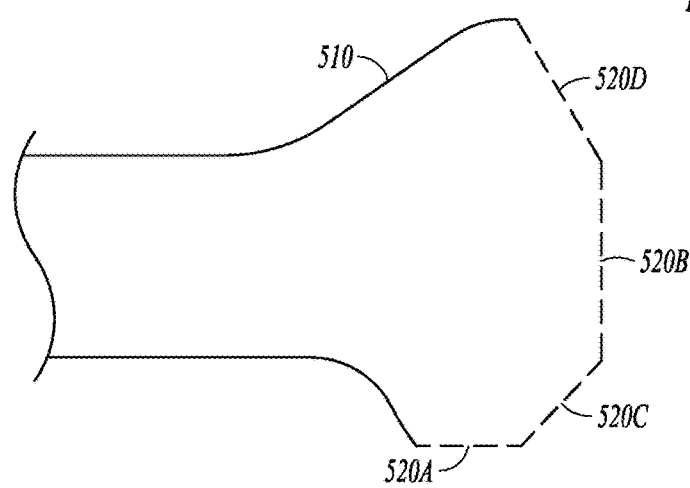
FIGS. 5A-C illustrate an example of selecting a set of guide members and generating an ordered sequence of bone cuts on a target bone.
Figure 5B:
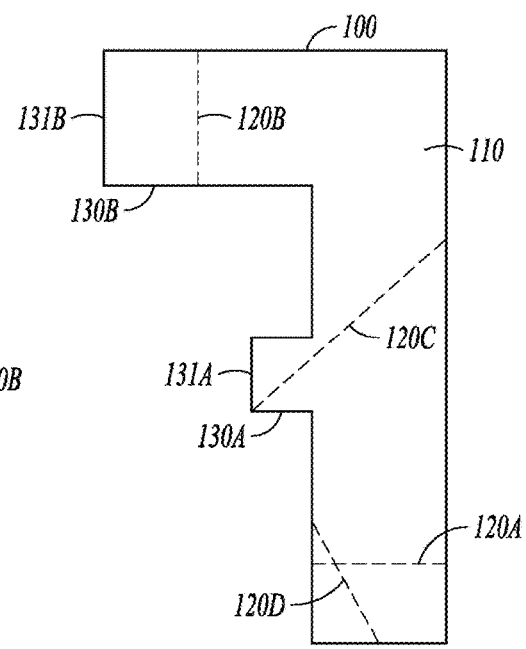
Figure 5C:
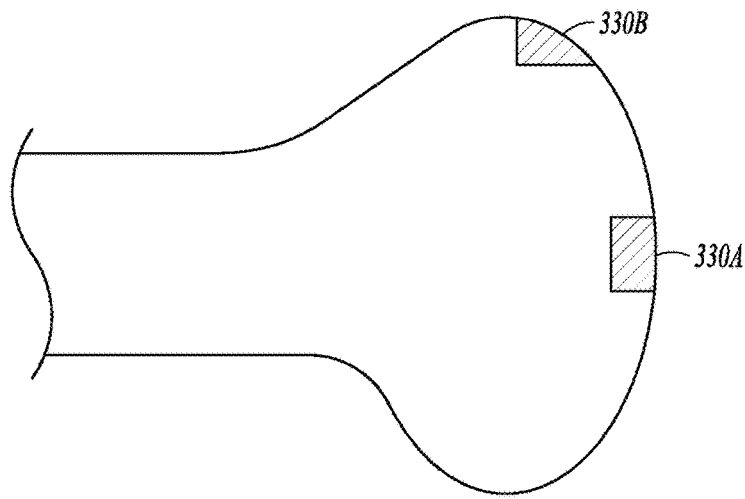

FIGS. 5A-C illustrate an example of selecting a set of guide members and generating an ordered sequence of bone cuts along the trajectories associated with the selected guide members. FIG. 5A illustrates a registered generic post-operative bone model 510, which can be an embodiment of $M^*_{post-op}$. The model 510 has desired resection surface representations defined by flat facets 520A-D. The resection surface representations can be derived from a plurality of images of post-operative bones having comparable anatomical origin from a group of subjects. Alternatively, the resection surface representations can be computer-simulated representations created based on the shape of the surfaces 550A-D of the bone implant to be interfaced with the resected target bone.

The orientations of the flat facets 520A-D can be compared to the cutting trajectories of the available guide members 120A-D on the cut guide 100, as illustrated in FIG. 5B. The flat facets 520A-D are determined to match the trajectories defined by guide members 120A-D, respectively; hence the guide members 120A-D can be selected for bone cutting. Although in this example all guide members 120A-D available in the cut guide 100 are selected, in other examples where the cut guide includes multiple or redundant guide members, only a subset rather than all of the available guide members are necessarily selected to match the orientation of the desired bone cuts. In some examples, two or more guide members having parallel trajectories can be selected, and the bone cuts can be executed along the parallel trajectories one at a time to progressively resect the target bone in multiple layers.

An ordered bone cut sequence can be decided by comparing the locations, sizes, shapes, volumes, or other geometric or morphological descriptors of the coupling receptacles and the cutting trajectories of the selected guide members 120A-D. For example, the trajectories of the guide members 120A and 120C shown in FIG. 5B are farther away from, and therefore less likely to interfere with, the coupling receptacles at the landing sites 330A and 330B as illustrated in FIG. 5C. The trajectory of the guide member 120B is close to, and is likely to interfere with, the landing site 330A. The trajectory of the guide member 120D is close to, and is likely to interfere with, both the landing sites 330A and 330B. Therefore, bone cuts along the trajectories associated with 120A-C can be performed first, the trajectory associated with 120B next, and the trajectory associated with 120D the last.

Figure 6:
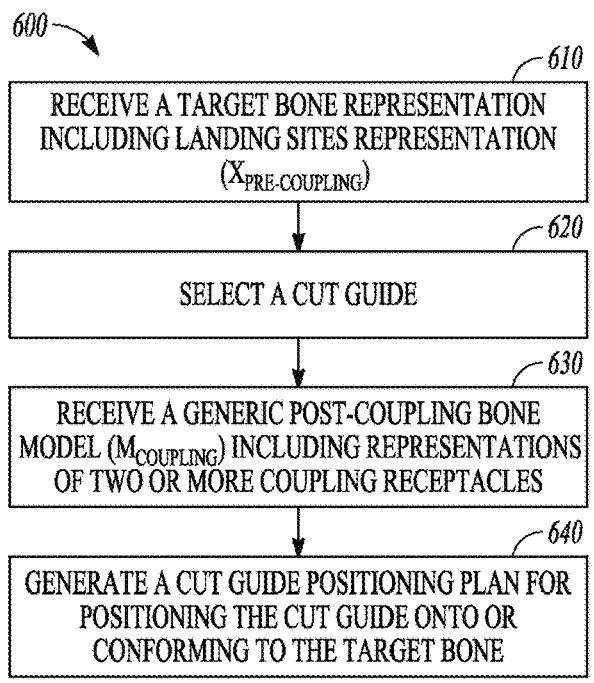
FIG. 6 is a flowchart that illustrates an example of a method for positioning a cut guide onto a target bone.

FIG. 6 is a flowchart that illustrates an example of a method 600 for operating a system to generate a cut guide positioning plan for positioning a cut guide onto a target bone. In an embodiment, the cut guide 100 and the cut guide positioning system 200, including their respective various embodiments discussed in this document, can be configured to perform method 600, including its various embodiments discussed in this document.

The method 600 can begin at 610 with receiving a representation of a target bone, such as by using the input interface 220. The target bone, such as a portion of a femur, a tibia, or other bone or articulation in the body, can be scheduled for surgical alteration, resection, or repair. The target bone representation includes two or more landing sites on the target bone, such as surfaces of an acetabulum, a proximal or distal extremity of a femur, or a proximal or distal extremity of a tibia. The target bone representation $X_{pre-coupling}$ can include a data set representing the shape, appearance, contour, or other geometric or morphological characteristics of the target bone. The target bone representation can also include intensity information. The representation $X_{pre-coupling}$ can include one of more of a medical image, a point cloud, a parametric model, or other morphological description of the target bone. Examples of medical images can include an X-ray, an ultrasound image, a computed tomography (CT) scan, a magnetic resonance (MR) image, a positron emission tomography (PET) image, a single-photon emission computed tomography (SPECT) image, or an arthrogram, among other 2D or 3D images.

At 620, a cut guide can be selected such as by a cut guide selection module. The cut guide can be selected based on the size, shape, anatomy, and mechanical properties of the target bone, such that the selected cut guide can be appropriately used in assisting bone cuts on the target bone. The selected cut guide, such as the cut guide 100, can include one or more guide members on the body of the cut guide with predetermined cutting trajectories, and a plurality of landing members each including a respective coupling feature configured to removably couple to a landing site of the target bone.

At 630, a generic post-coupling bone model ($M_{coupling}$) is received, such as by using the model receiver module 210. The model $M_{coupling}$ may be derived from a plurality of images of bones taken from a group of subjects, where the images can have anatomical origin similar to the target bone representation $X_{pre-coupling}$. The model $M_{coupling}$ can be in a form of a parametric model, a statistical model, a shape-based model such as a statistical shape model, a volumetric model, an elastic model, a geometric spine model, or a finite element model. In addition to the representation of the shape and morphology of the bone, the model $M_{coupling}$ can include representations of two or more coupling receptacles produced at respective two or more landing sites on the bone. An example of the coupling receptacle includes recessed portions created at specified landing sites on the target bone. Each coupling receptacle is sized, shaped or otherwise configured to receive and secure the respective coupling feature of the landing members on the cut guide. The representations of the two or more coupling receptacles can include indications of the location on the model $M_{coupling}$, size, shape, volume, or other geometric or morphological descriptors. In an embodiment, the coupling receptacle representation can be computer-simulated based on the size, shape, volume, or other geometric or morphological descriptors of the coupling features on the landing members of the cut guide. The computer-simulated coupling receptacle representations can be added to the coupler-free normal bone model to create a post-coupling bone model $M_{coupling}$.

At 640, a cut guide positioning plan for positioning the cut guide onto or conforming to the target bone is generated, such as by using the navigation-based guide coupling preparation system 230. To generate the cut guide positioning plan, the generic post-coupling bone model $M_{coupling}$ can be registered to the target bone representation $X_{pre-coupling}$ to create a registered post-coupling model $M^*_{coupling}$. In one embodiment, the registration includes a process of segmentation, model transformation, and matching and alignment between the target bone representation and the transformed or registered model. The bone model $M_{coupling}$ and the target bone representation $X_{pre-coupling}$ can each be partitioned into a plurality of segments representing various anatomical structures on the respective image. The portion of the $M_{coupling}$ that contains the coupling receptacle representation can be differentiated from other portions of the $M_{coupling}$ free of coupling receptacle representation, and a registration area free of coupling receptacle representation can be identified from the segments of the $M_{coupling}$. Using a comparison between the coupler-free segment of $M_{coupling}$ and the corresponding segments of $X_{pre-coupling}$, a desired transformation can be determined which minimizes the difference between the identified coupling receptacle-free segments on the $M_{coupling}$ and the corresponding segments of $X_{pre-coupling}$. The desired transformation can then be applied to the model $M_{coupling}$ to create the registered post-coupling model $M^*_{coupling}$. One or more segments of the registered post-coupling model $M^*_{coupling}$ can then be matched to the corresponding registration area of the $X_{pre-coupling}$, and the remaining segments of the registered post-coupling model $M^*_{coupling}$ can be aligned with the remaining segments of the target bone representation $X_{pre-coupling}$ based on the matching.

The registered post-coupling model $M^*_{coupling}$ can then be compared to the target bone representation $X_{pre-coupling}$ to determine the landing sites for creating the two or more coupling receptacles, and to determine size, shape, and other geometric or morphological descriptors of the coupling receptacles. The landing sites of the coupling receptacles can also be determined using information about the cut guide, including size and shape of the coupling features of the landing members, and the cutting trajectories associated with the guide members.

The cut guide positioning plan can be used by a system, such as the cut guide positioning system 200, for locating the landing sites on the target bone, and controlling a surgical cutting tool to produce two or more coupling receptacles to desired size and shape at the landing sites. The surgical cutting tool, such as a surgical drill, a surgical mill, a surgical saw, or other surgical equipment, can be manually operated or driven by an automated computer-controlled system. The cut guide can therefore be positioned onto or conform to the target bone via the established coupling between the coupling features on the cut guide and the coupling receptacles created on the target bone.

To ensure tight and secure coupling, the method 600 can optionally include an operation of processing the interfacing surfaces of the coupling receptacle to allow for an interference fit in at least one dimension between the coupling features and the coupling by compression or by friction. The amount of interference can be produced at the coupling receptacle to achieve desired tightness of fit. The positioning can be performed manually by an operator or with the assist of an automated system such as a computer-controlled robotic arm. Examples of methods for creating the coupling receptacle in accordance with the cut guide positing plan are discussed below, such as with reference of FIG. 7.

In some embodiments, the method 600 can further includes providing audio, visual, or other multi-media presentations of the post-coupling bone model $M_{coupling}$, the registered post-coupling model $M^*_{coupling}$, the target bone representation, among other things. The presentation can be displayed on a monitor or other communication interface. The presentation formats can also include sound, dialog, text, 2D or 3D graphs, or animations to assist an end-user such as a surgeon during the process of creating and evaluating the cut guide positioning plan. Presentation of the coupling between the target bone model and the cut guide, including a measurement of relative positions between the coupling feature and the respective coupling receptacle, can also be provided to the end-user when the cut guide is positioned onto or conform to the target bone.

Figure 7:
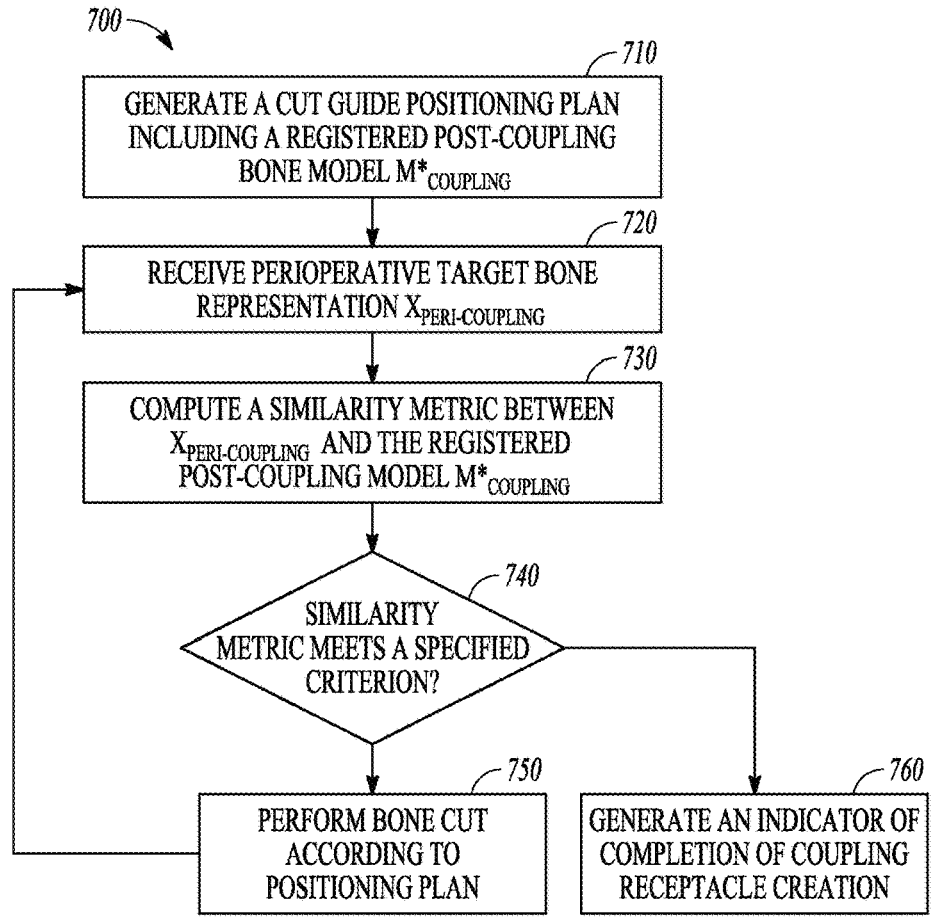
FIG. 7 is a flowchart that illustrates an example of a method for producing coupling receptacles on the target bone.

FIG. 7 is a flowchart that illustrates an example of a method 700 for producing coupling receptacles on a target bone. The method 700 can be used for progressively creating bond couplers using a navigation-based feedback-controlled mechanism. The method 700 can be an embodiment of producing coupling receptacles on the target bone at 650 in method 600.

A cut guide positioning plan, including a registered post-coupling bone model $M^*_{coupling}$, is generated at 710. The cut guide positioning plan and the post-coupling bone model $M^*_{coupling}$ can be generated using the steps 610-640 in the method 600. At 720, a perioperative target bone representation $X_{peri-coupling}$ can be received. The perioperative target bone representation $X_{peri-coupling}$ can include a data set representing the target bone with two or more coupling receptacles during the coupling receptacle creation process. Prior to the coupling receptacle creating, the perioperative target bone representation $X_{peri-coupling}$ can be initialized to the target bone representation $X_{pre-coupling}$.

At 730, a similarity metric between the coupling receptacles on the model $M^*_{coupling}$ and the corresponding perioperative coupling receptacles on the representation $X_{peri-coupling}$ is computed. In an embodiment, statistical or morphological features representing sizes, shapes, volume, or other geometric or morphological descriptors of the coupling receptacles can be extracted from $M^*_{coupling}$ and $X_{peri-coupling}$. Similarity metric can be computed using the statistical or morphological features of the model $M^*_{coupling}$ and those of the representation $X_{peri-coupling}$. Examples of the similarity metric can include L1 norm, L2 norm (Euclidian distance), infinite norm, or other norm in the normed vector space. The similarity metric can also include correlation coefficient, mutual information, or ratio image uniformity.

The similarity metric can be provided to the operator such as a surgeon via a displaying module, or to an automated computer-controlled system. At 740, the similarity metric can be compared to specified criterion such as a predetermined threshold value. If the similarity metric fails to meet the specified criterion, the coupling receptacle creation process continues at 750 with further bone cut according to the positioning plan, and peri-operative bone representation can be re-generated at 720. The navigation-based feedback-controlled coupling receptacle creation process then continues. If, however, the similarity metric meets the specified criterion, the perioperative coupling receptacles on $X_{peri-coupling}$ are deemed substantially similar to the desired coupling receptacles on the model $M^*_{coupling}$. An indicator can then be generated to indicate a completion of the coupling receptacle creation process at 760.

Figure 8:
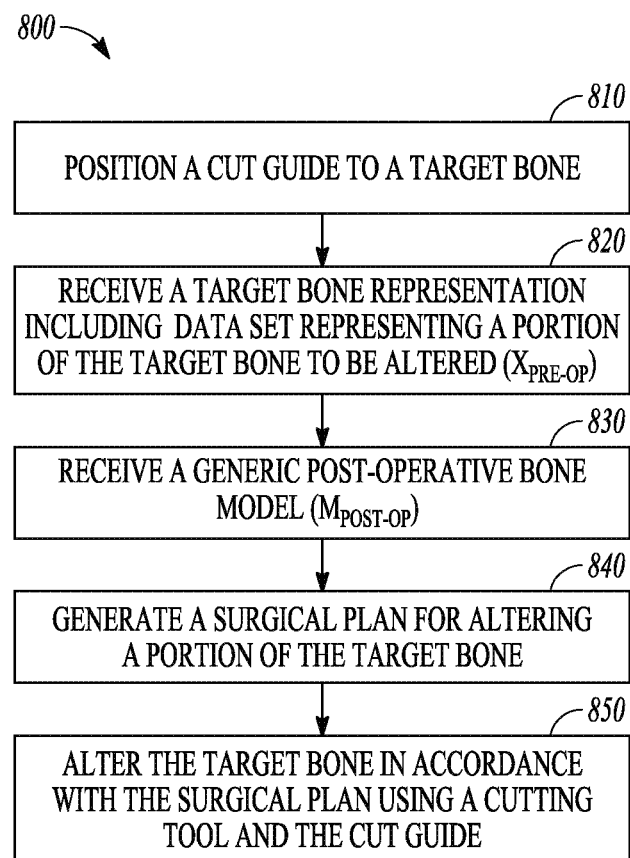
FIG. 8 is a flowchart that illustrates an example of a method for resecting a portion of a target bone using a cut guide.

FIG. 8 is a flowchart that illustrates an example of a method 800 for resecting a portion of a target bone using a cut guide. In an embodiment, the cut guide 100 and the orthopedic surgical system 400, including their respective various embodiments discussed in this document, can be configured to perform method 800, including its various embodiments discussed in this document.

At 810, a cut guide, such as the cut guide 100, can be positioned onto a target bone. In an embodiment, positioning the cut guide can be performed using the method 600. A target bone representation ($X_{pre-op}$) is received at 820. The representation $X_{pre-op}$ can include a data set representing a portion of the target bone to be altered. For example, the representation $X_{pre-op}$ can include a medical image, a point cloud, a parametric model, or other morphological description of the target bone. In some embodiments, the $X_{pre-op}$ can include a representation of the target bone following the creation of the coupling receptacles.

At 830, a generic post-operative bone model ($M_{post-op}$) is received. The model $M_{post-op}$ can include a data set representing a post-operative bone (i.e., after the bone cut) having an anatomical origin comparable to the target bone. The model $M_{post-op}$ can be in a form of a parametric model, a statistical model, a shape-based model such as a statistical shape model, or a volumetric model. In an example, the model $M_{post-op}$ can be derived from a plurality of images of post-operative bones of comparable anatomical origin from a group of subjects. Alternatively, at least a portion of the post-operative bone model $M_{post-op}$, such as the resection surfaces that interface with an implant, can be computer-simulated representation of the post-operative bone surface.

At 840, a surgical plan for altering a portion of the target bone can be created when the cut guide is securely positioned onto or conforms to the target bone. The post-operative bone model $M_{post-op}$ can be registered to the representation $X_{pre-op}$ to create a registered post-operative bone model $M^*_{post-op}$. Similar to the process of registering the generic post-coupling bone model $M_{coupling}$ to the target bone representation $X_{pre-coupling}$ as discussed above in FIG. 6, the registration can include a process of segmentation, model transformation, and matching and alignment between $X_{pre-op}$ and $M^*_{post-op}$. In particular, after portioning the model $M_{post-op}$ and the pre-operative bone representation $X_{pre-op}$ each into a plurality of segments, the generic post-coupling bone model $M_{post-op}$ can be transformed to create a registered post-operative bone model $M^*_{post-op}$, such as using a comparison between the segment of the $M_{post-op}$ free of resection surface representation and the corresponding segments of the $X_{pre-op}$. One or more segments of the registered post-operative bone model $M^*_{post-op}$ can then be matched to the corresponding registration area of the $X_{pre-op}$. The remaining segments of the registered post-operative bone model $M^*_{post-op}$ can be aligned with the remaining segments of $X_{pre-op}$ based on the matching.

A surgical plan can then be generated using the registered post-operative model $M^*_{post-op}$ for cutting the target bone until the altered target bone is in substantial conformity with the registered post-operative model $M^*_{post-op}$. The orientations of the desired resection surface as defined by the registered post-operative model $M^*_{post-op}$ can be compared to the cutting trajectories of the guide members of the cut guide. One or more guide members that match the orientation of a portion of the resection surface can then selected. An ordered sequence of bone cuts along the trajectories associated with the selected guide members is then determined. The cutting sequence can be determined using the anatomical, geometric, physical and mechanical properties of the portions of the bone to be altered. The cutting sequence can also be scheduled considering the locations, sizes, shapes, volumes, or other geometric or morphological descriptors of the coupling receptacles relative to the cutting trajectories. For example, the bone cuts along the cutting trajectories that are spatially farther away from the coupling receptacles can be executed earlier (i.e., at the front of the sequence), the bone cuts along the cutting trajectories that are spatially closer to the coupling receptacles can be executed later (i.e., at a latter part of the sequence), and the bone cuts along the cutting trajectories that intersect with one or more coupling receptacles can be executed last (i.e., at the end of the sequence). The ordered bone cuts as such allow the cut guide to remain securely attached to the target bone while performing bone cuts, and prevent a bone cut from interfering with the coupling between the cut guide and the target bone.

The target bone can then be altered at 850 in accordance with the surgical plan. A cutting tool can be positioned in the selected guide members of the cut guide and resect portions of the target bone along the cutting trajectories in the determined ordered sequence. Bone cutting can be performed manually by an operator or with the assist of an automated system such as a computer-controlled robotic arm. In some examples, the method 800 can further include presenting, on a display module or a communication interface, audio, visual, or other multi-media presentations of one or more of the data set representing the portion of the target bone to be altered ($X_{pre-op}$), the generic post-operative bone model ($M_{post-op}$), the selected guide members on the cut guide, and the scheduled sequence of bone cuts along the cutting trajectories, among other things.

Figure 9:
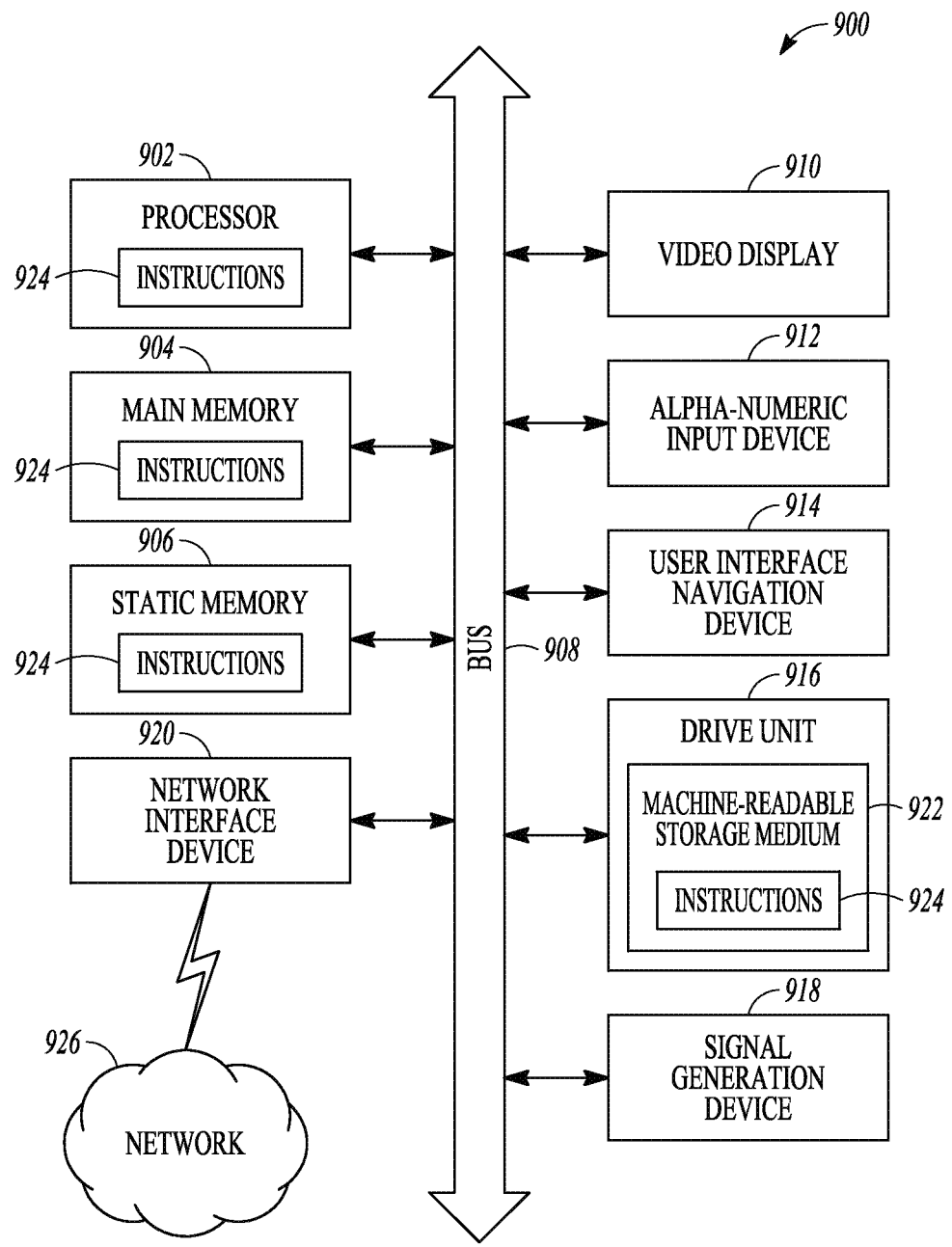
FIG. 9 is a block diagram that illustrates an example of a computer system within which instructions for causing the computer system to perform bone cut positioning may be executed.

FIG. 9 is a block diagram that illustrates an example of a machine in the form of a computer system 900 within which instructions, for causing the computer system to perform any one or more of the methods discussed herein, may be executed. In various embodiments, the machine can operate as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a PDA, a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 900 includes a processor 902 (such as a central processing unit (CPU), a graphics processing unit (GPU), or both), a main memory 904 and a static memory 906, which communicate with each other via a bus 908. The computer system 900 may further include a video display unit 910 (such as a liquid crystal display (LCD) or a cathode ray tube (CRT)), an alpha-numeric input device 912 (such as a keyboard), a user interface (UI) navigation device (or cursor control device) 914 (such as a mouse), a disk drive unit 916, a signal generation device 918 (e.g., a speaker) and a network interface device 920.

The disk drive unit 916 includes a machine-readable storage medium 922 on which is stored one or more sets of instructions and data structures (e.g., software) 924 embodying or used by any one or more of the methods or functions described herein. The instructions 924 may also reside, completely or at least partially, within the main memory 904, static memory 906, and/or within the processor 902 during execution thereof by the computer system 900, the main memory 904 and the processor 902 also constituting machine-readable media. In an example, the instructions 924 stored in the machine-readable storage medium 922 include instructions causing the computer system 900 to receive a target bone representation including a data set representing two or more landing sites of the target bone ($X_{pre-coupling}$), to select a cut guide configured to be adjustably positionable onto or otherwise to conform to the target bone, and to receive a generic post-coupling bone model ($M_{coupling}$) including a data set representing a bone having the two or more coupling receptacles. The instructions 924 can also store the instructions 924 that cause the computer system 900 to generate a cut guide positioning plan for positioning the cut guide onto or conforming to the target bone.

The machine-readable storage medium 922 may further store the instructions 924 that cause the computer system 900 to produce, respectively at the two or more landing sites, the two or more coupling receptacles sized, shaped or otherwise configured to receive and secure the respective coupling feature of each of the plurality of landing members, and to attach the cut guide to the landing site of the target bone by respectively engaging the coupling features with the coupling receptacles. The instructions in the machine-readable storage medium 922 may also cause the computer system 900 to receive a target bone representation including a data set representing a portion of the target bone to be altered, receive a generic post-operative bone model including a data set representing a post-operative bone having an anatomical origin comparable to the target bone, generate a surgical plan for altering a portion of the target bone when the cut guide is securely positioned onto or otherwise conforms to the target bone, and alter the target bone in accordance with the surgical plan using the cutting tool and the cut guide.

While the machine-readable medium 922 is shown in an example embodiment to be a single medium, the term "machine-readable medium" may include a single medium or multiple media (e.g., a centralized or distributed database, and/or associated caches and servers) that store the one or more instructions or data structures. The term "machine-readable storage medium" shall also be taken to include any tangible medium that is capable of storing, encoding or carrying instructions for execution by the machine and that cause the machine to perform any one or more of the methods of the present invention, or that is capable of storing, encoding or carrying data structures used by or associated with such instructions. The term "machine-readable storage medium" shall accordingly be taken to include, but not be limited to, solid-state memories, and optical and magnetic media. Specific examples of machine-readable media include non-volatile memory, including by way of example, semiconductor memory devices (e.g., erasable programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks. A "machine-readable storage medium" shall also include devices that may be interpreted as transitory, such as register memory, processor cache, and RAM, among others. The definitions provided herein of machine-readable medium and machine-readable storage medium are applicable even if the machine-readable medium is further characterized as being "non-transitory." For example, any addition of "non-transitory," such as non-transitory machine-readable storage medium, is intended to continue to encompass register memory, processor cache and RAM, among other memory devices.

In various examples, the instructions 924 may further be transmitted or received over a communications network 926 using a transmission medium. The instructions 924 may be transmitted using the network interface device 920 and any one of a number of well-known transfer protocols (e.g., HTTP). Examples of communication networks include a LAN, a WAN, the Internet, mobile telephone networks, plain old telephone (POTS) networks, and wireless data networks (e.g., Wi-Fi and WiMAX networks). The term "transmission medium" shall be taken to include any intangible medium that is capable of storing, encoding or carrying instructions for execution by the machine, and includes digital or analog communications signals or other intangible media to facilitate communication of such software.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A machine-readable storage medium including instructions that, when executed by a machine, cause the machine to:
receive a target bone representation including a data set representing two or more landing sites of the target bone ($X_{pre\text{-}coupling}$);
select a cut guide configured to be adjustably positionable onto or otherwise to conform to the target bone, the cut guide including (1) a guide body having one or more guide members sized, shaped or otherwise configured to guide a cutting tool along a respective cutting plane, and (2) a plurality of landing members, each of the plurality of landing members including a respective coupling feature extending from the guide body and configured to removably couple to the target bone via two or more coupling receptacles created on the target bone;
receive a generic post-coupling bone model ($M_{coupling}$) including a data set representing a bone having the two or more coupling receptacles; and
generate a cut guide positioning plan for positioning the cut guide onto or conforming to the target bone by:
registering $M_{coupling}$ to $X_{pre\text{-}coupling}$ to create a registered generic post-coupling bone model,
determining, using the registered generic post-coupling bone model, the two or more landing sites of the target bone for creating the two or more coupling receptacles and geometric or morphological descriptors of the two or more coupling receptacles, and
providing one or more of:
the data set representing the two or more landing sites of the target bone ($X_{pre\text{-}coupling}$),
the generic post-coupling bone model ($M_{coupling}$),
the landing site of the target bone, or
the size, shape, and geometric or morphological descriptors of the two or more coupling receptacles on the target bone.

2. The machine-readable storage medium of claim 1, wherein the instruction causing the machine to determine the two or more landing sites includes causing the machine to determine locations of the two or more landing sites on the target bone using information including size and shape of the coupling features of the plurality of landing members and the cutting trajectories relative to the target bone.

3. The machine-readable storage medium of claim 1, further comprising instructions that cause the machine to:
receive a target bone representation including a data set representing a portion of the target bone to be altered ($X_{pre\text{-}op}$);
receive a generic post-operative bone model ($M_{post\text{-}op}$) including a data set representing a post-operative bone having an anatomical origin comparable to the target bone;
generate a surgical plan for altering a portion of the target bone when the cut guide is securely positioned onto or otherwise conforms to the target bone; and
alter the target bone in accordance with the surgical plan using the cutting tool and the cut guide.

4. The machine-readable storage medium of claim 3, wherein the instruction causing the machine to generate the surgical plan includes causing the machine to:
register $M_{post\text{-}op}$ to $X_{pre\text{-}op}$ and create a registered generic post-operative bone model;
select one or more guide members using the registered generic post-operative bone model; and
schedule a sequence of bone cuts along the cutting trajectories associated with the selected one or more guide members when the coupling features of the cut guide are coupled to the coupling receptacles of the target bone.

5. The machine-readable storage medium of claim 3, wherein the instruction causing the machine to receive $X_{pre\text{-}op}$ includes causing the machine to receive a mathematical descriptive model or a two-dimensional or three-dimensional graphical model of the target bone, and wherein the instruction causing the machine to receive $M_{post\text{-}op}$ includes causing the machine to receive a mathematical descriptive model or a two-dimensional or three-dimensional graphical model of the post-operative bone.

6. The machine-readable storage medium of claim 1, further comprising instructions that cause the machine to:
produce, respectively at the two or more landing sites, the two or more coupling receptacles sized, shaped or otherwise configured to receive and secure the respective coupling feature of each of the plurality of landing members; and
attach the cut guide to the landing site of the target bone by respectively engaging the coupling features with the coupling receptacles,
wherein the instruction causing the machine to produce a coupling receptacle includes causing the machine to produce a recessed portion at the landing site of the target bone, the recessed portion sized, shaped or otherwise configured to receive and secure the protruding portion of the respective coupling feature of each of the plurality of landing members.

7. The machine-readable storage medium of claim 6, wherein the instruction causing the machine to produce the recessed portion includes causing the machine to generate a recess creation plan including geometric or morphological descriptors of the recessed portion, and to create the recessed portion using a surgical tool in accordance with the recess creation plan.

8. The machine-readable storage medium of claim 1, further comprising instructions that cause the machine to:
receive a peri-operative target bone representation including a data set representing the size, shape, volume, or other geometric or morphological descriptors of the coupling receptacle of the target bone ($X_{peri\text{-}coupling}$);
determine a similarity metric between the coupling receptacle on the registered generic post-coupling bone model and the corresponding perioperative coupling receptacle on the perioperative target bone representation $X_{peri\text{-}coupling}$;
generate an indication of completion of the coupling receptacle preparation in response to the similarity metric meeting a specified criterion; and
display the peri-operative target bone representation $X_{peri\text{-}coupling}$, the similarity metric, and the indication of the completion of the coupling receptacle preparation.

9. The machine-readable storage medium of claim 1, further comprising instructions that cause the machine to display one or more of:
- the generic post-coupling bone model ($M_{coupling}$);
- the registered generic post-coupling bone model;
- the generic post-operative bone model ($M_{post-op}$);
- the selected guide members on the cut guide; and
- the scheduled sequence of bone cuts along the cutting trajectories.

10. A machine-readable storage medium including instructions that, when executed by a machine, cause the machine to:
- receive a target bone representation including a data set representing two or more landing sites of the target bone ($X_{pre-coupling}$);
- select a cut guide configured to be adjustably positionable onto or otherwise to conform to the target bone, the cut guide including (1) a guide body having one or more guide members sized, shaped or otherwise configured to guide a cutting tool along a respective cutting plane, and (2) a plurality of landing members, each of the plurality of landing members including a respective coupling feature extending from the guide body and configured to removably couple to the target bone via two or more coupling receptacles created on the target bone;
- generate a generic post-coupling bone model ($M_{coupling}$) including a data set representing a bone having the two or more coupling receptacles and one or more of geometric characteristics of the bone and intensity information of the bone; and
- generate a cut guide positioning plan for positioning the cut guide onto or conforming to the target bone by:
  - registering $M_{coupling}$ to $X_{pre-coupling}$ to create a registered generic post-coupling bone model,
  - determining, using the registered generic post-coupling bone model, the two or more landing sites of the target bone for creating the two or more coupling receptacles and geometric or morphological descriptors of the two or more coupling receptacles, and
  - providing one or more of:
    - the data set representing the two or more landing sites of the target bone ($X_{pre-coupling}$),
    - the generic post-coupling bone model ($M_{coupling}$),
    - the landing site of the target bone, or
    - the size, shape, and geometric or morphological descriptors of the two or more coupling receptacles on the target bone.

11. The machine-readable storage medium of claim 10, wherein the one or more of the geometric characteristics of the bone and the intensity information of the bone are constructed from a plurality of medical images of bones of comparable anatomical origin from a plurality of subjects.

12. The machine-readable storage medium of claim 10, wherein the instruction causing the machine to determine the two or more landing sites includes causing the machine to determine locations of the two or more landing sites on the target bone using information including size and shape of the coupling features of the plurality of landing members and the cutting trajectories relative to the target bone.

13. The machine-readable storage medium of claim 10, further comprising instructions that cause the machine to:
- receive a target bone representation including a data set representing a portion of the target bone to be altered ($X_{pre-op}$);
- receive a generic post-operative bone model ($M_{post-op}$) including a data set representing a post-operative bone having an anatomical origin comparable to the target bone;
- generate a surgical plan for altering a portion of the target bone when the cut guide is securely positioned onto or otherwise conforms to the target bone; and
- alter the target bone in accordance with the surgical plan using the cutting tool and the cut guide.

14. The machine-readable storage medium of claim 13, wherein the instruction causing the machine to generate the surgical plan includes causing the machine to:
- register $M_{post-op}$ to $X_{pre-op}$ and create a registered generic post-operative bone model;
- select one or more guide members using the registered generic post-operative bone model; and
- schedule a sequence of bone cuts along the cutting trajectories associated with the selected one or more guide members when the coupling features of the cut guide are coupled to the coupling receptacles of the target bone.

15. The machine-readable storage medium of claim 13, wherein the instruction causing the machine to receive $X_{pre-op}$ includes causing the machine to receive a mathematical descriptive model or a two-dimensional or three-dimensional graphical model of the target bone, and wherein the instruction causing the machine to receive $M_{post-op}$ includes causing the machine to receive a mathematical descriptive model or a two-dimensional or three-dimensional graphical model of the post-operative bone.

16. The machine-readable storage medium of claim 10, further comprising instructions that cause the machine to:
- produce, respectively at the two or more landing sites, the two or more coupling receptacles sized, shaped or otherwise configured to receive and secure the respective coupling feature of each of the plurality of landing members; and
- attach the cut guide to the landing site of the target bone by respectively engaging the coupling features with the coupling receptacles,
- wherein the instruction causing the machine to produce a coupling receptacle includes causing the machine to produce a recessed portion at the landing site of the target bone, the recessed portion sized, shaped or otherwise configured to receive and secure the protruding portion of the respective coupling feature of each of the plurality of landing members.

17. The machine-readable storage medium of claim 16, wherein the instruction causing the machine to produce the recessed portion includes causing the machine to generate a recess creation plan including geometric or morphological descriptors of the recessed portion, and to create the recessed portion using a surgical tool in accordance with the recess creation plan.

18. The machine-readable storage medium of claim 10, further comprising instructions that cause the machine to:
- receive a peri-operative target bone representation including a data set representing the size, shape, volume, or other geometric or morphological descriptors of the coupling receptacle of the target bone ($X_{peri-coupling}$);
- determine a similarity metric between the coupling receptacle on the registered generic post-coupling bone model and the corresponding perioperative coupling receptacle on the perioperative target bone representation $X_{peri-coupling}$;

generate an indication of completion of the coupling receptacle preparation in response to the similarity metric meeting a specified criterion; and display the peri-operative target bone representation $X_{peri\text{-}coupling}$, the similarity metric, and the indication of the completion of the coupling receptacle preparation.

19. The machine-readable storage medium of claim 10, further comprising instructions that cause the machine to display one or more of:

the generic post-coupling bone model ($M_{coupling}$);
the registered generic post-coupling bone model;
the generic post-operative bone model ($M_{post\text{-}op}$);
the selected guide members on the cut guide; and
the scheduled sequence of bone cuts along the cutting trajectories.

* * * * *